United States Patent
Sebring

(10) Patent No.: US 9,968,314 B1
(45) Date of Patent: May 15, 2018

(54) STEERABLE X-RAY IMAGING DETECTOR MODULE

(71) Applicant: Sebring Mechanical Design, Inc., Townsend, MA (US)

(72) Inventor: J. Paul Sebring, Townsend, MA (US)

(73) Assignee: Sebring Mechanical Design, Inc., Townsend, MA (US)

(*) Notice: Subject to any disclaimer, the term of this patent is extended or adjusted under 35 U.S.C. 154(b) by 311 days.

(21) Appl. No.: 14/997,857

(22) Filed: Jan. 18, 2016

Related U.S. Application Data

(60) Provisional application No. 62/147,079, filed on Apr. 14, 2015.

(51) Int. Cl.
*A61B 6/00* (2006.01)
*G01T 1/24* (2006.01)

(52) U.S. Cl.
CPC .......... *A61B 6/4233* (2013.01); *A61B 6/4291* (2013.01); *A61B 6/4452* (2013.01); *A61B 6/587* (2013.01); *G01T 1/243* (2013.01)

(58) Field of Classification Search
CPC ....... A61B 6/42; A61B 6/4233; A61B 6/4291; A61B 6/4429; A61B 6/4452; A61B 6/587; G01T 1/16; G01T 1/20; G01T 1/243; G01T 1/244
See application file for complete search history.

(56) References Cited

U.S. PATENT DOCUMENTS

| | | | |
|---|---|---|---|
| 4,592,080 A * | 5/1986 | Rauch | A61B 6/4275 378/19 |
| 4,872,191 A | 10/1989 | Bernardi | |
| 5,991,357 A | 11/1999 | Marcovici et al. | |
| 6,693,291 B2 | 2/2004 | Nelson et al. | |
| 6,744,053 B2 | 6/2004 | Wong et al. | |
| 7,177,387 B2 | 2/2007 | Yasunaga et al. | |
| 7,236,560 B2 | 6/2007 | Malamud | |
| 8,287,187 B2 | 10/2012 | Miller | |
| 8,314,412 B2 | 11/2012 | Vogtmeier | |
| 8,453,512 B2 | 6/2013 | Sasso et al. | |
| 8,483,353 B2 | 7/2013 | Hoffman et al. | |
| 8,525,119 B2 | 9/2013 | Luhta et al. | |
| 2012/0049074 A1* | 3/2012 | Luhta | G01T 1/2985 250/366 |
| 2012/0093288 A1* | 4/2012 | Mastronardi | G01N 23/04 378/57 |
| 2014/0050296 A1 | 2/2014 | Ying | |
| 2014/0219415 A1 | 8/2014 | Ying | |
| 2014/0355734 A1 | 12/2014 | Ying | |

* cited by examiner

*Primary Examiner* — Glen Kao
(74) *Attorney, Agent, or Firm* — Iandiorio Teska & Coleman, LLP

(57) ABSTRACT

An X-ray system includes a plurality of X-ray detector modules and a backbone for positioning the detector modules relative to an X-ray source. A mount for each detector module is coupled to the backbone. One or more actuators extend between the mount and the detector module for individually adjusting the detector module relative to the mount for aligning the detector module. A plate with a rocker member may be attached behind each module and the mount then includes a frame with cradle surfaces for the rocker member.

24 Claims, 16 Drawing Sheets

Scatter effects without anti-scatter device

STEERABLE X-RAY IMAGING DETECTOR MODULE

RELATED APPLICATIONS

This application claims benefit of and priority to U.S. Provisional Application Ser. No. 62/147,079 filed Apr. 14, 2015, under 35 U.S.C. §§ 119, 120, 363, 365, and 37 C.F.R. § 1.55 and § 1.78, which is incorporated herein by this reference.

BACKGROUND OF THE INVENTION

In X-ray CT systems, X-rays are used to image the internal structure and features of a region of a subject or an object. The imaging is performed by an X-ray CT system which images internal structure and features of a plurality of thin planar slices or a 3D volume of a region of an object using X-rays. For medical applications, the imaging objects include human bodies. An X-ray CT system generally comprises an X-ray source that provides a cone-shaped X-ray beam and an array of closely spaced X-ray detectors that face the X-ray source.

The X-ray source and array of detectors are typically mounted in a gantry so that a patient/object being imaged with the CT system, generally lying on an appropriate support couch, can be positioned within the gantry between the X-ray source and the array of detectors. The gantry and couch are moveable relative to each other so that the X-ray source and detector array can be positioned axially at desired locations along the patient's body. The gantry comprises a stationary structure referred to as a stator and a rotary element referred to as a rotor which is mounted to the stator so that the rotor is rotatable about the axial direction. In third generation CT systems, the X-ray source and detectors are mounted on the rotor. Angular positions of the rotor about the axial direction are controllable so that the X-ray source can be positioned at desired angles, referred to as view angles, around a patient's body. To image a slice in a region of a patient's body, the X-ray source is positioned at the axial position of the slice and the X-ray source is rotated around the slice to illuminate the slice with X-rays from a plurality of different view angles. At each view angle, detectors in the array of detectors generate signals responsive to the intensity of X-rays from the source that pass through the slice. The signals are processed to determine the amounts by which X-rays from the X-ray source are attenuated over various path lengths through the slice that the X-rays traverse in passing though the slice from the X-ray source to the detectors. The amounts by which the X-rays are attenuated are used to determine an X-ray absorption coefficient of materials in the slice as a function of position in the slice. The absorption coefficient is used to generate an image of the slice and identify compositions and densities of tissues in the slice.

The X-ray detectors comprised in a detector array of CT system are generally packaged in a plurality of modules, known as detector-modules, each of which comprises a plurality of X-ray detectors. Most modern CT systems are multi-slice CT systems designed to simultaneously image a plurality of slices of a patient. The X-ray detectors in each CT detector-module of a multi-slice scanner are arranged in a rectangular matrix of rows and columns. The X-ray detector matrices of any two CT detector-modules in a CT system are substantially identical and comprise a same number of rows of detectors and a same number of columns of detectors. The modules are positioned one adjacent to and contiguous with the other in a closely packed array with their rows of detectors aligned end to end so that the X-ray detectors form a plurality of long parallel rows of X-ray detectors.

A multi-slice X-ray CT system is usually named or featured by the maximum number of slices that it can simultaneously image, for example, an 8-slice CT system means that it can simultaneously image at most 8 slices; a 16-slice CT system can simultaneously image at most 16 slices.

The X-ray detectors in each long row of detectors lie on an arc of a circle having its center located at a focal point of the CT system's X-ray source and the design of these detectors is specifically determined by the radius of the circle which is hereinafter referred to as the focal distance. The design of X-ray detectors placed on the arc of one focusing distance of one CT system cannot therefore be used on another CT system of a different focusing distance.

X-ray detectors typically include a plurality of anti-scatter grids for collimating X-ray beams received at the detector. The grids are comprised of thin septa of a high Z material to absorb off axis X-rays not intended to the scintillator pixel below the grid opening. The grid openings converge at the focal spot of the X-ray source. Below the grid there is a scintillator for converting X-rays to light energy, and attached to the back of the scintillator, photodiodes for receiving the light energy and producing electric charges there from. The anti-scatter grids are aligned and bounded with the elements of the scintillator arrays to very tight and exact locational tolerances. Each of the X-ray detector modules are accurately aligned on a backbone to focus on the focal spot of the X-ray source.

The X-rays typically are generated from the focal spot in the X-ray tube and collimated to project a conical beam of the required size onto an array of the multi-pixel detectors on the opposite side of the object being imaged. The ideal image is generated if the X-ray photons coming from the focal spot, through the object, and onto the detector travel in a straight line. Because the imaged objects can contain disperse dense materials, bone, metal, etc., that reflect or scatter the X-ray photons, the scattered photons travel at some arbitrary angle and can enter the detector array in some other location than their initial trajectory would have had them enter. The result is X-ray photons with no useful information of the imaged object creating background noise by diluting the photons that contain image information decreasing signal to noise. As the noise increases the image quality degrades.

To help absorb the unwanted scattered photons it is typical to add some type of thin guiding plate, tunnels or shielding material made of X-ray absorbent shielding material made of lead, tungsten, etc. between each row of pixels, aligned on edge to the detector face. The shielding plates are critically aligned with the taper of the X-ray beam and only allow the X-rays that are aligned with the local angle of the X-ray beam and if functioning correctly only allow the X-rays that are aligned with the focal spot to enter the detector. In some cases the signal to noise (SNR) can be reduced by adding additional absorbing plates orthogonal to the initial plates creating a 2D plate (anti-scatter grid) that encloses each pixel of the detector to further exclude off-axis photons.

To increase resolution of imaging the detector pixels need to be made smaller, resulting in higher density with less space between each pixel requiring the shielding be more closely spaced. If the anti-scatter grid is increased in height, towards the X-ray source to increase effectiveness and if it is precisely aligned it will absorb more off-axis X-ray photons increasing SNR.

As the anti-scatter grid height increases it also makes alignment of the detector with regard to the focal spot more critical. If the system and its related tolerances can't hold or predict if one detector in the array is reliably aimed at the focal spot then the result can be shadowing of the X-ray photons, and degradation of the image data.

Another factor is that as the X-ray tube heats the focal spot shifts some unpredictable amount creating more shadowing and further degrading images.

The following U.S. patents and published applications are incorporated herein by this reference: U.S. Pat. Nos. 4,872, 191; 5,991,357; 6,693,291; 6,744,053; 7,177,387; 7,236, 560; 8,287,187; 8,483,353; 8,314,412; 8,525,119; 2012/ 0049074; 2014/0050296; 2014/0219415; and 2014/ 0355734.

BRIEF SUMMARY OF THE INVENTION

In the invention, the detectors can be mounted as an array in a flat panel or curvilinear array of a flat segment with each detector fixed to a flexure or pivot. A piezoelectric or other actuator mounted effectively on the detector can tip or tilt the detector module to actively aim it at the X-ray source, or move it X-Y, or combinations of these motions. The anti-scatter grid will move with the detector. An initial scan or scout scan with nothing in the X-ray field may be made and the detector modules individually are adjusted to sense the greatest X-ray intensity from the source. Then this position information can be stored in a look up table that can be updated, by dithering, looking for the max/min readings, or calibration scans.

Featured is an X-ray system comprising a plurality of X-ray detector modules and a backbone for positioning the detector modules relative to an X-ray source. A mount for each detector module is coupled to the backbone. One or more actuators extend between the mount and the detector module for individually adjusting the detector module relative to the mount for aligning the detector module. A plate with a rocker member may be attached behind each module and the mount then includes a frame with cradle surfaces for the rocker member. In one design, a Y-motion actuator extends between the frame and the rocker member and a tip actuator extends between the plate and the frame for pivoting the rocker member in the cradle surfaces.

The system may further include one or more actuators between the frame and the backbone for moving the frame and module relative to the backbone. In one design, a tilt actuator extends between the frame and the backbone for adjusting the frame relative to the backbone and a Z-axis actuator is located in a backbone socket for adjusting the frame relative to the backbone. The frame may include a seat with a post received in the backbone socket.

In another design the mount, module, and the actuators are configured as a Stewart platform. For example, a plate is coupled to the detector module and a frame member is coupled to the backbone with the actuators extending between the plate and the frame. Typically, the X-ray detector module includes a 2-D anti-scatter grid, scintillator material, and a photodiode array.

Also featured is an X-ray system detector module steering system comprising a mount for the detector module attachable to a backbone and one or more actuators configured to adjust the detector module relative to the mount and/or to adjust the mount relative to the backbone. The mount and actuators may be configured to adjust the module relative to the mount and/or to adjust the mount relative to the backbone.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
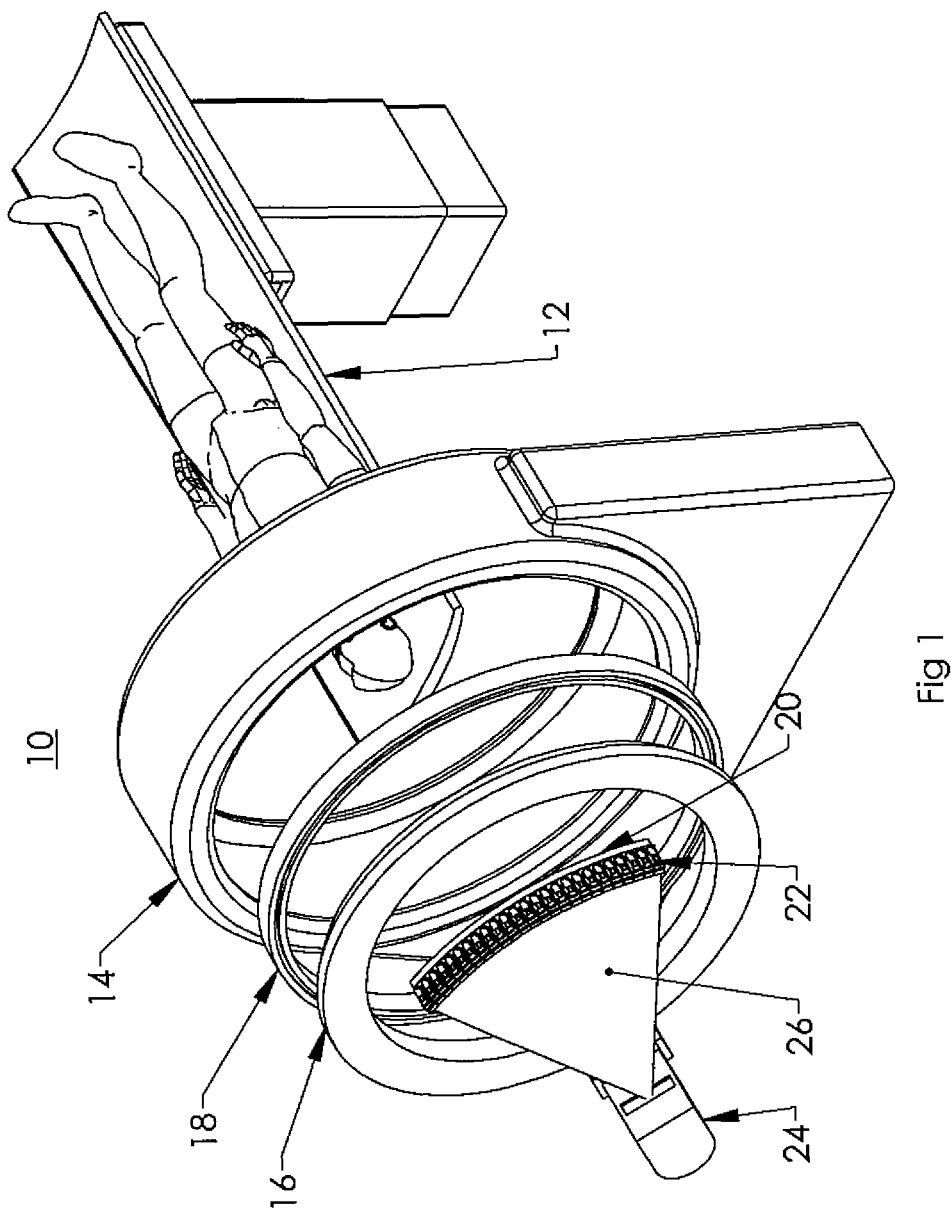
FIG. 1 is a schematic exploded view of a CT imaging system.

Various objects, features and advantages of the invention will occur to those skilled in the art from the following description of a preferred embodiment and the accompanying drawings. But, aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the invention is not to be limited to that embodiment.

Figure 2:
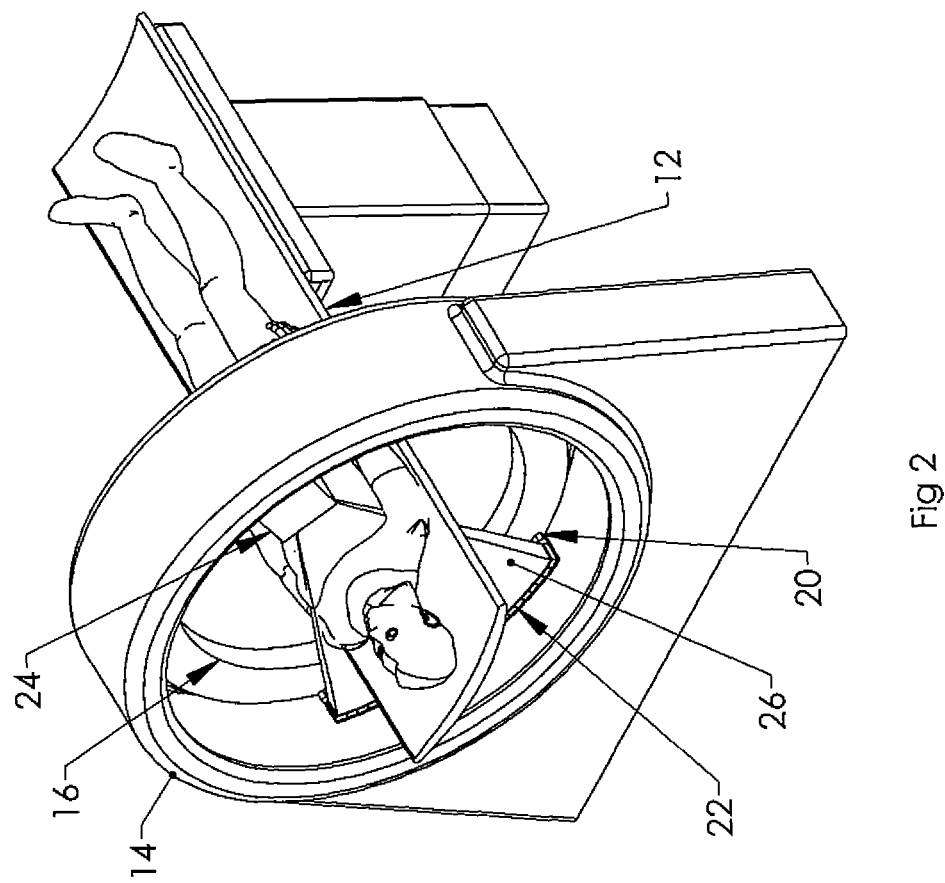
FIG. 2 is a another view of the CT imaging system of FIG. 1.

FIG. 1 is a simplified view of a CT imaging system 10. Patient support table 12 is shown. The basic imaging and structural components include gantry 14, rotor 16, bearing 18, and backbone 20 supporting detector array 22. X-ray source 24 produces fan beam 26. As shown in FIG. 2, the CT imaging system functions by rotating the imaging components about the rotor support bearing axis. The X-rays generated by the X-ray tube are directed at the imaging receptors or modules. The patient is moved through the rotating beam in the Z direction (patient long axis) at an accurately controlled rate. X-ray image slices of the anatomy of interest are captured and through software and converted into 3D imagery.

Figure 3:
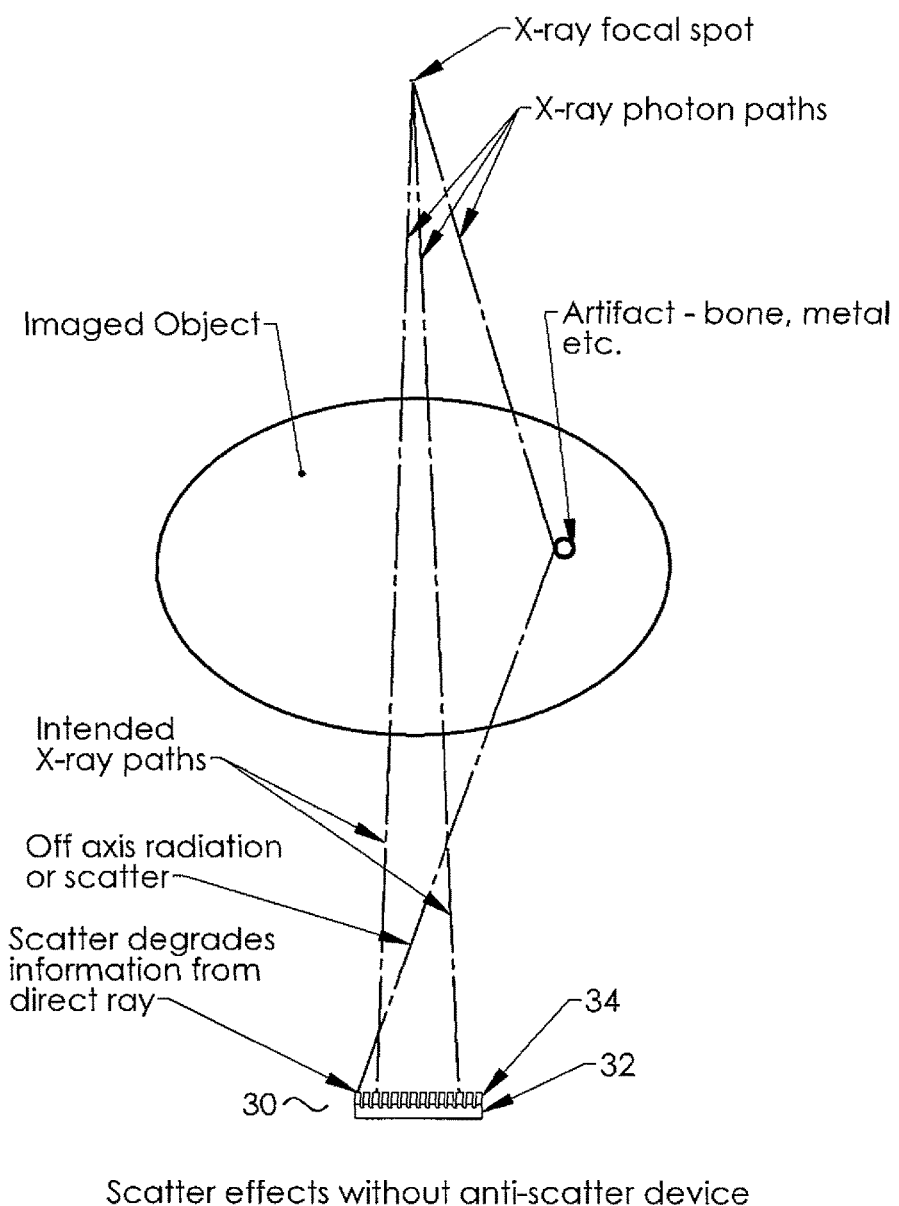
FIG. 3 shows the scatter effects of X-rays without an anti-scatter device associated with the X-ray module.

FIG. 3 demonstrates X-rays projecting in a straight line unless forced or scattered in alternate directions when encountering disperse dense matter. The scattered or off-axis rays can enter a detector module in other than the intended location. The scatter can degrade the image by weakening the signal coming from the intended rays. Here, the detector module 30 includes photodiode board 32 and scintillator crystal 34.

Figure 4:
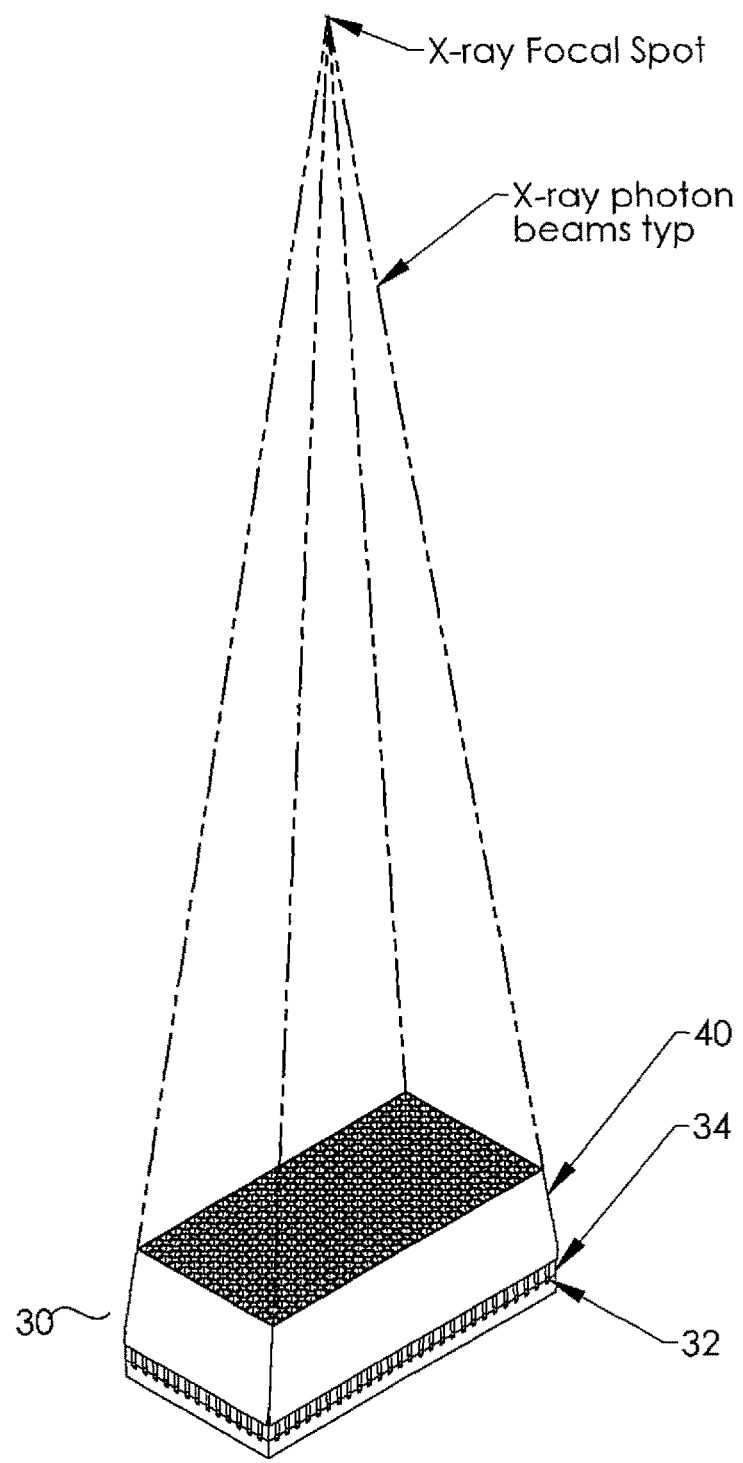
FIG. 4 shows an X-ray detector module with a 2-D anti-scatter grid.
Figure 5:
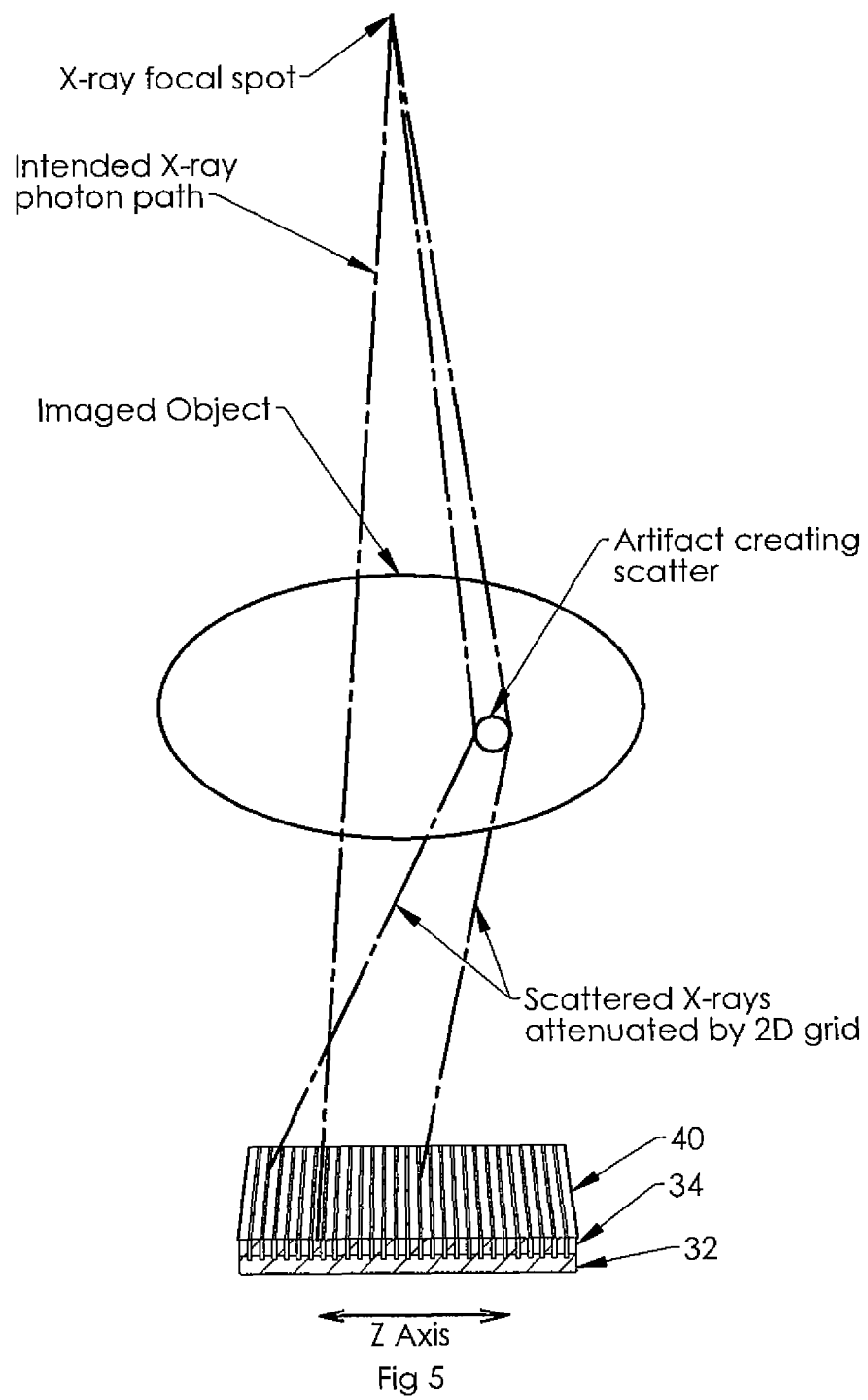
FIG. 5 depicts the off axis X-rays attenuated or blocked by the addition of the anti-scatter device.

FIG. 4 shows a 2D anti-scatter grid 40 attached to a scintillator and photodiode array for module 30. See U.S. Pat. No. 8,287,187 incorporated here by this reference. This assembly forms what is known at the detector module. The scintillator, when exposed to X-rays, will convert the X-ray energy into light. The photodiodes, attached to the underside of the scintillator convert the light into an electrical signals which through data processing can be used to generate images. As shown in FIG. 5, the off-axis X-rays can be attenuated or blocked by adding an anti-scatter device 40 known as a grid. The drawing demonstrates the scattered rays being blocked from the scintillator array. Only the intended X-rays (X-rays containing information of imaged object) are allowed to enter the scintillator blocking the unintended rays increasing image resolution.

Figure 6:
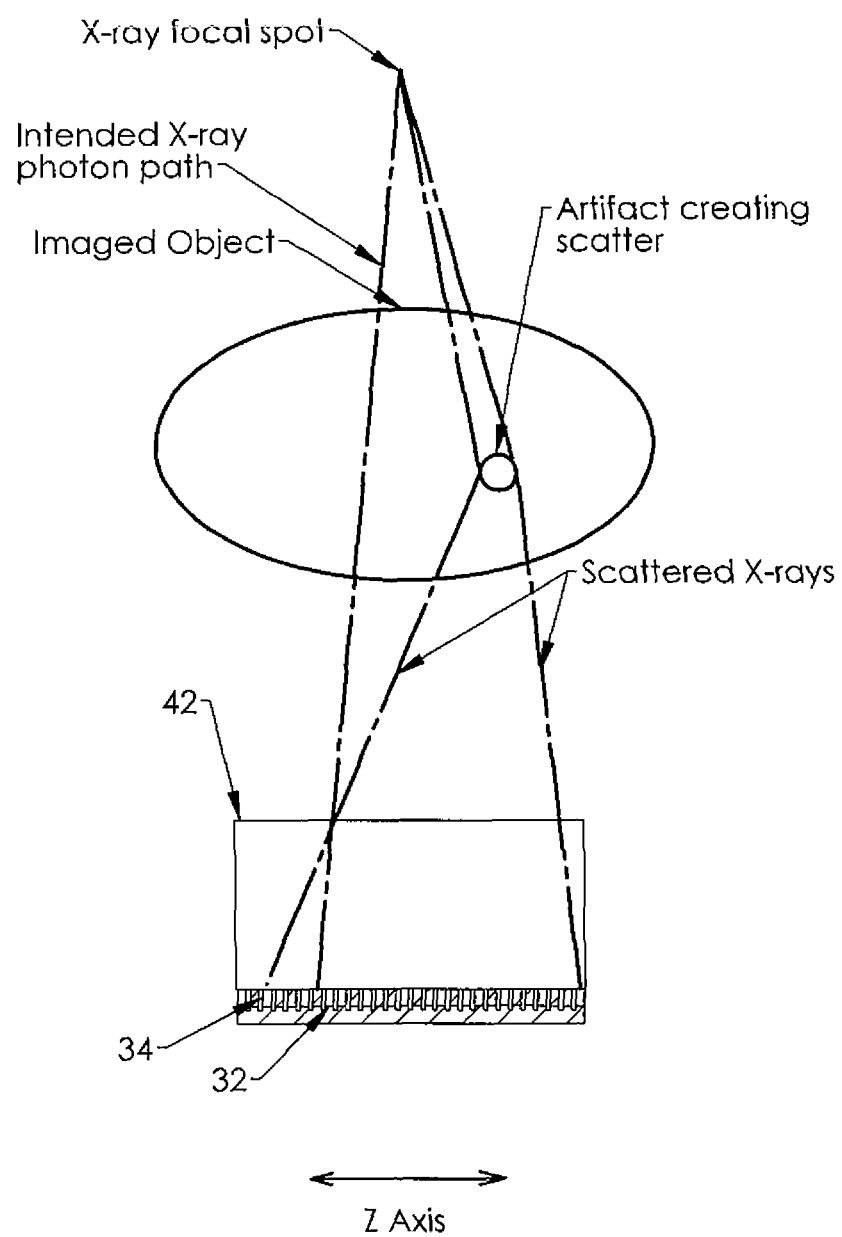
FIG. 6 shows a one-dimensional grid scatter plate.

FIG. 6 demonstrates the limited functionality of a 1 dimensional grid scatter plate 42 only placed in line with the Z axis. In this type of anti-scatter device, there is no anti scatter plates in the Z direction. This means there can be scatter in that direction degrading images. Most CT imaging systems use a 1D grid as it is less expensive and the technology to construct a fine 2D grid did not exist until recently.

Figure 7:
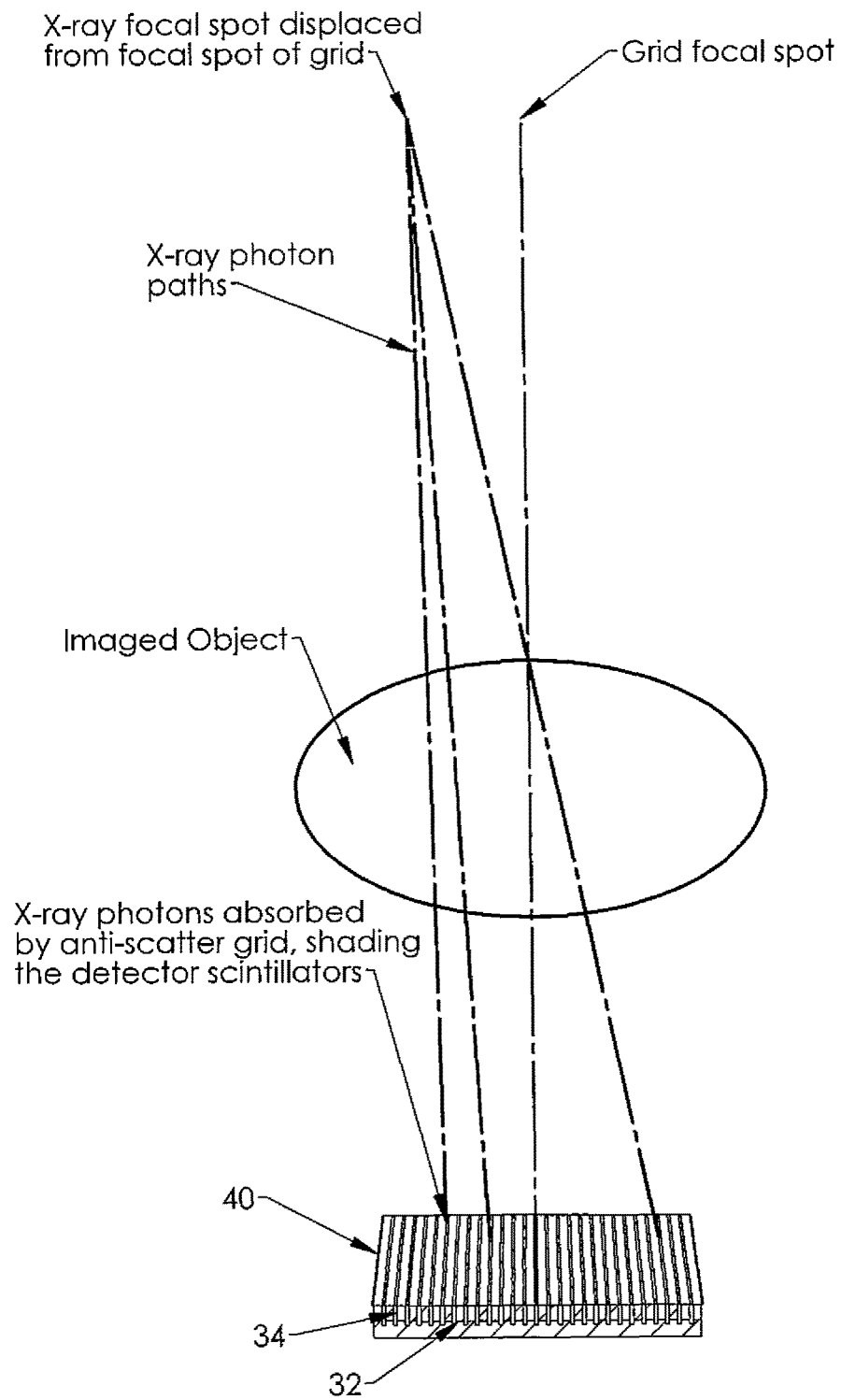
FIG. 7 shows an alignment shift in the X-ray focal spot which results in shadowing of the detector degrading or eliminating the ability to generate images.

FIG. 7 demonstrates an alignment shift in the X-ray focal spot which results in shadowing of the detector degrading or eliminating the ability to generate images.

Figure 8:
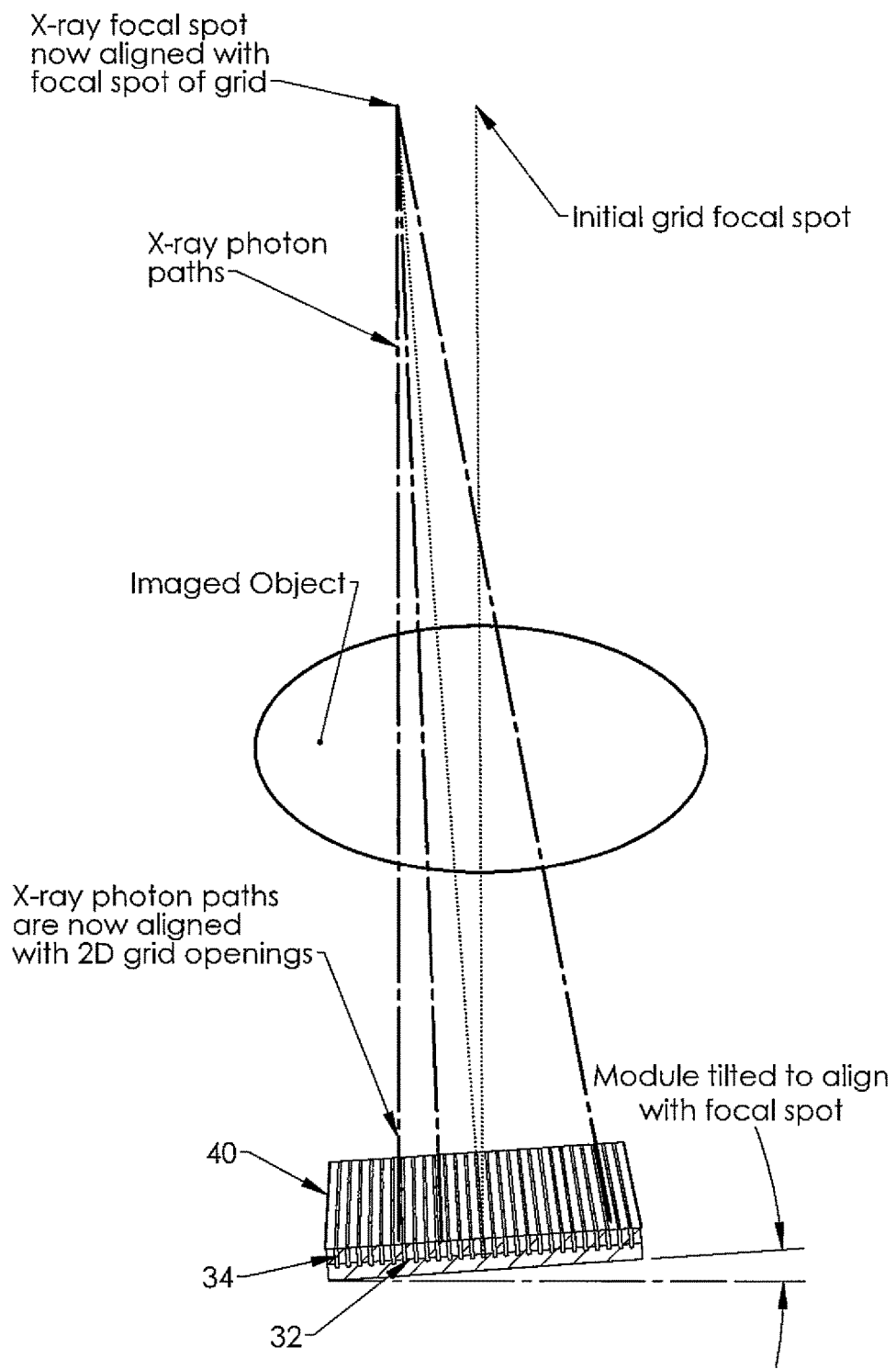
FIG. 8 shows the tilting of the detector module for alignment with the X-ray focal spot.

FIG. 8 shows that if the detector can be tilted or moved in some way back into alignment with the X-ray focal spot, the imaging functionality can be restored and improved. Only one axis of tilt is demonstrated in FIG. 8 but the preferred positioning ability disclosed herein is omni-directional.

Figure 9:
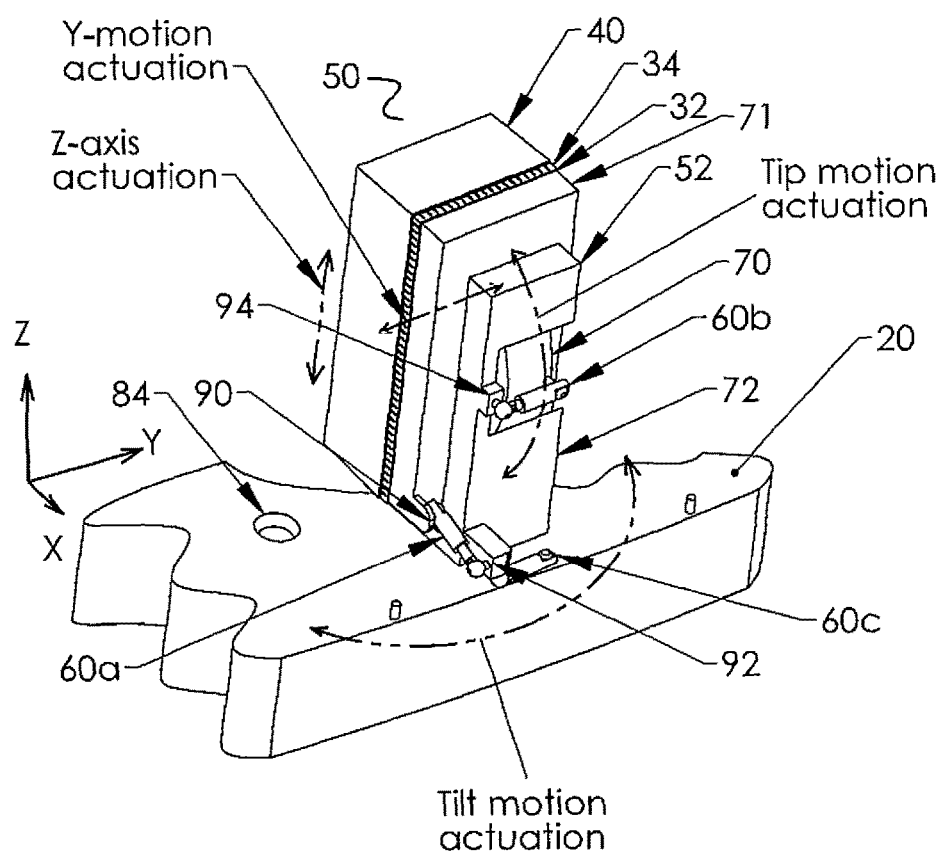
FIG. 9 is a schematic rear view of an example of a detector module mount in accordance with the invention.
Figure 10:
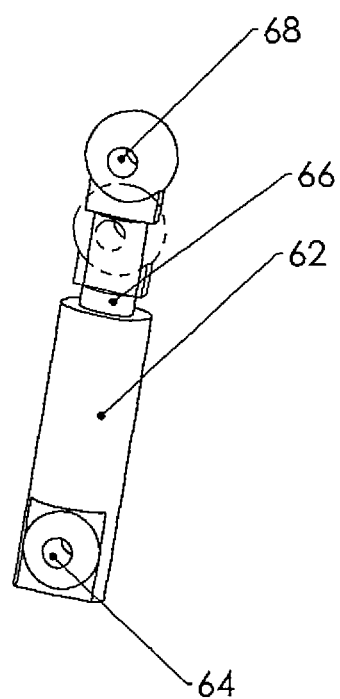
FIG. 10 is a schematic view of a preferred piezoelectric actuator for use with the detector module steering system.

As shown in FIG. 9, one preferred X-ray system includes a plurality of X-ray detector modules 50, a backbone 20 for positioning the modules relative to an X-ray source, and a mount 52 for each module. Here, the mount for each module is preferably configured to adjustably mount a module 50 with respect to the backbone 20. The module may be adjusted relative to the mount and also the mount (and hence the module) may be adjusted relative to the backbone. One or more actuators 60, FIG. 10 are configured for individually adjusting each module. A typical piezoelectric actuator includes cylinder 62 with pivot mount 64 and piston 66 extendable and retractable with respect to cylinder 62 and including pivot mount 68.

In one example, as shown in FIG. 9, a plate 71 with a rocker member 70 is added to the rear of each detector module. The rocker member 70 is received in a mount frame member 72 coupled to the backbone. This mount arrangement allows the rocker member 70 to tip relative to the frame member 72 which preferably includes front and rear angled cradle surfaces 76a and 76b, FIG. 11, cradling the rocker 70 and allowing it to pivot.

Figure 11:
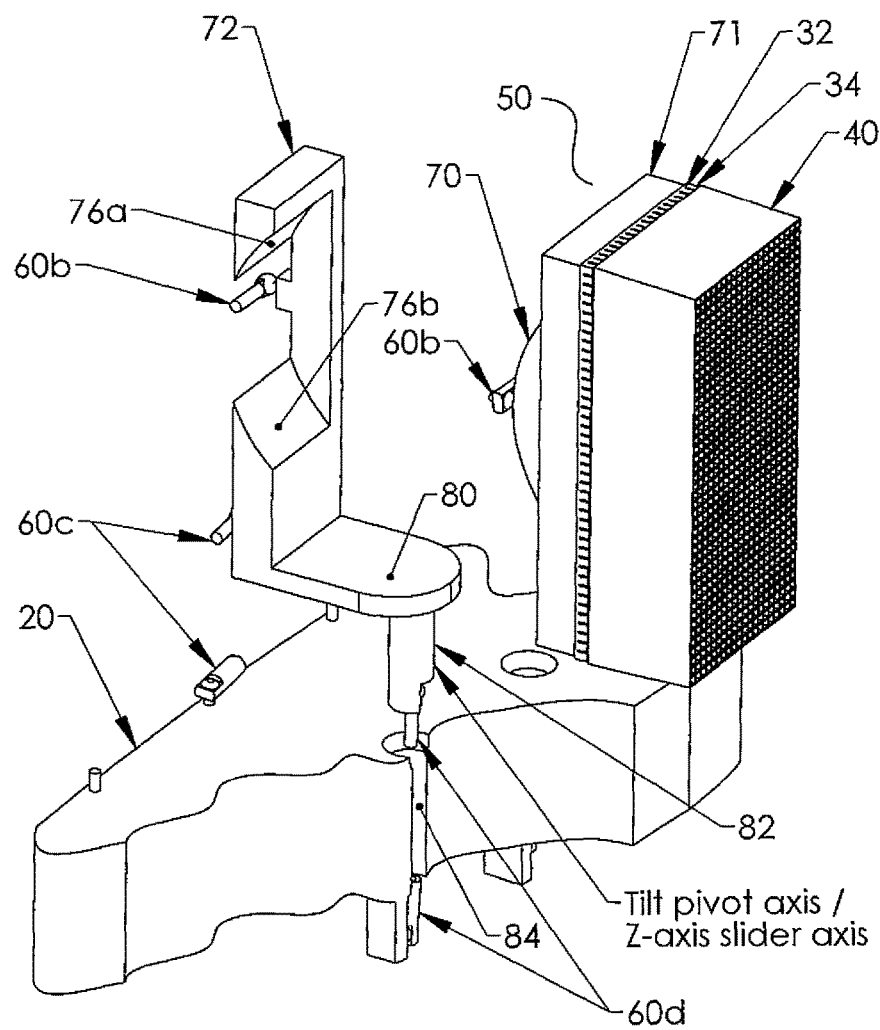
FIG. 11 is an exploded view of the detector mounting arraignment of FIG. 9.
Figure 12:
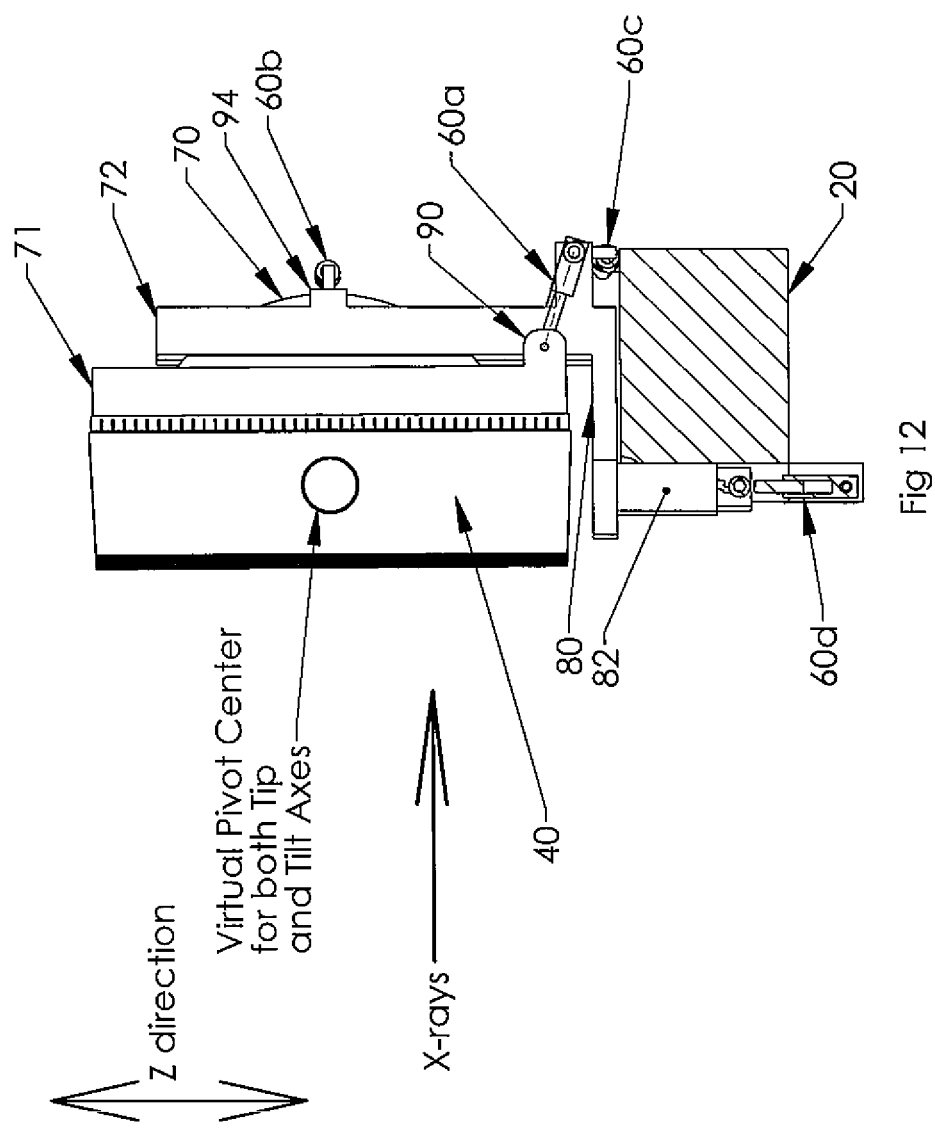
FIG. 12 is a schematic side view of the X-ray detector module mounting arrangement shown in FIGS. 9 and 11.

The group of actuators as shown in FIGS. 9 and 11 may include a tip actuator 60a pivotably connected between the frame member 72 and the module 50. A Y axis motion actuator 60b, if provided, is typically connected between the frame member 72 and the rocker member 60b for linearly moving the module relative to the frame member. A tilt actuator 60c, if included, is pivotably connected between the frame member 72 and the backbone 20 for tilting the detector module. The actuation motion provided by each actuator is shown in FIG. 9. The frame may further include a seat 80, FIG. 11. In a preferred embodiment shown, the seat 80 includes a post 82 extending therefrom received in a socket 84 in the backbone 20. In this way, a Z axis actuator 60d in the socket is pivotably connected between the post 82 and the backbone 20 to adjust the module in the Z axis direction as shown in FIGS. 11 and 12.

In one preferred embodiment, tip actuator 60a is pivotably coupled to ear 90 on plate 71 and block 92 on frame 72. Actuator 60a moves module 50 relative to frame 72. Tilt actuator 60c is pivotably coupled to frame block 92 and to backbone 20. Actuator 60c moves frame 72 relative to backbone 20. Y-motion actuator 60b is pivotably coupled to rocker 70 and pivotably coupled to block 94 on frame 72. Actuator 60b moves module 50 relative to frame 72. Z-axis actuator 60d, FIG. 11 moves frame 72 relative to backbone 20.

The result is the ability to tip or tilt the detector module to actively and independently aim it at the X-ray source focal spot. Any anti-scatter grid will move with the detector. A controller subsystem may be implemented with the X-ray system to automatically adjust the actuator(s) of each module to sense the greatest X-ray intensity from the source. The controller thus controls the activation of the actuator(s) and may be responsive to the output of the detectors. See also U.S. Pat. No. 8,453,512 incorporated herein by this reference.

Figure 13:
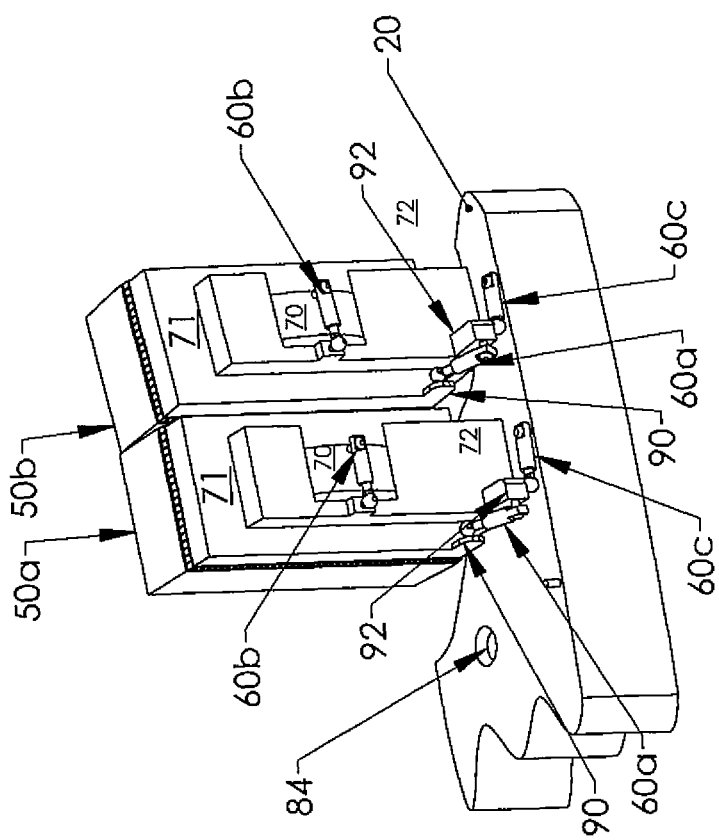
FIG. 13 is a schematic rear view showing two X-ray detector module assemblies steerably mounted to the backbone of an X-ray system.
Figure 14:
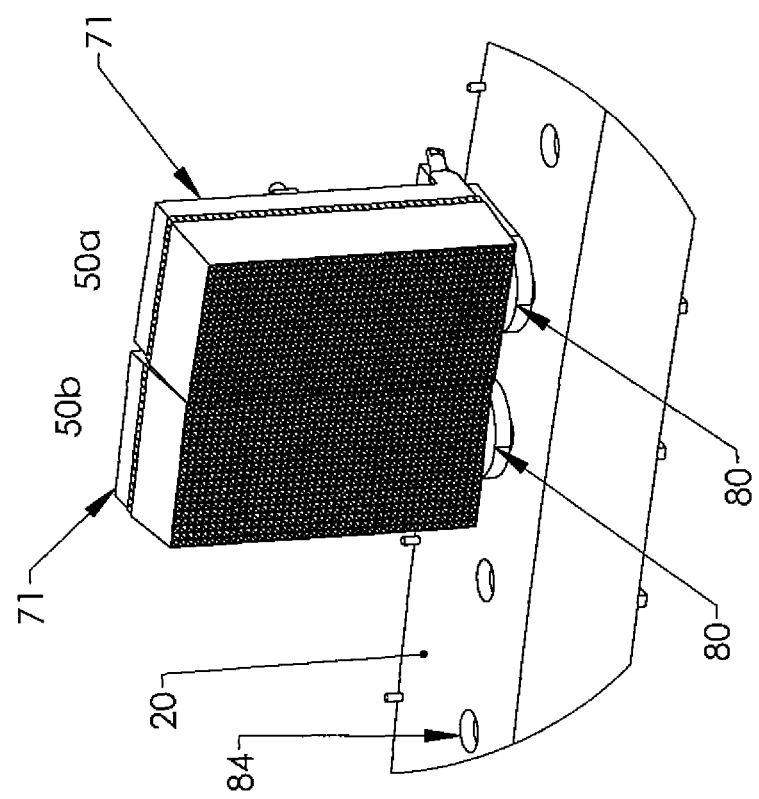
FIG. 14 is front view of the two X-ray detector modules shown in FIG. 13.

FIGS. 13-14 show two X-ray detector modules 50a and 50b which can be independently adjusted relative to backbone 20. Usually, there are numerous such detector modules.

Figure 15:
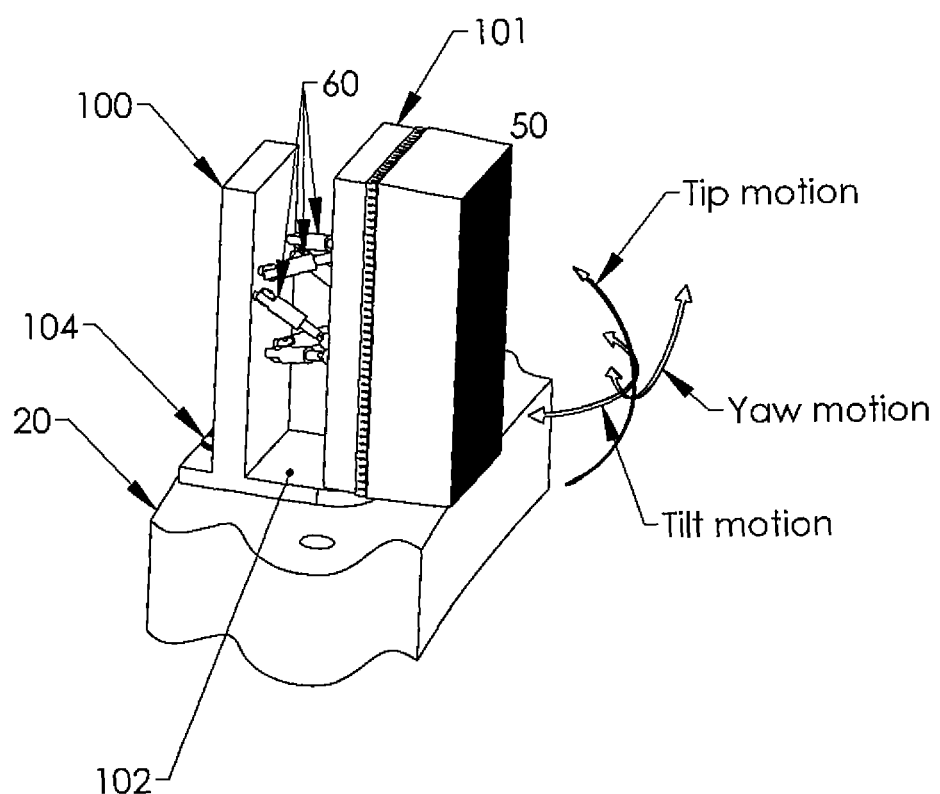
FIG. 15 is a schematic side view showing another X-ray module steering assembly.
Figure 16:
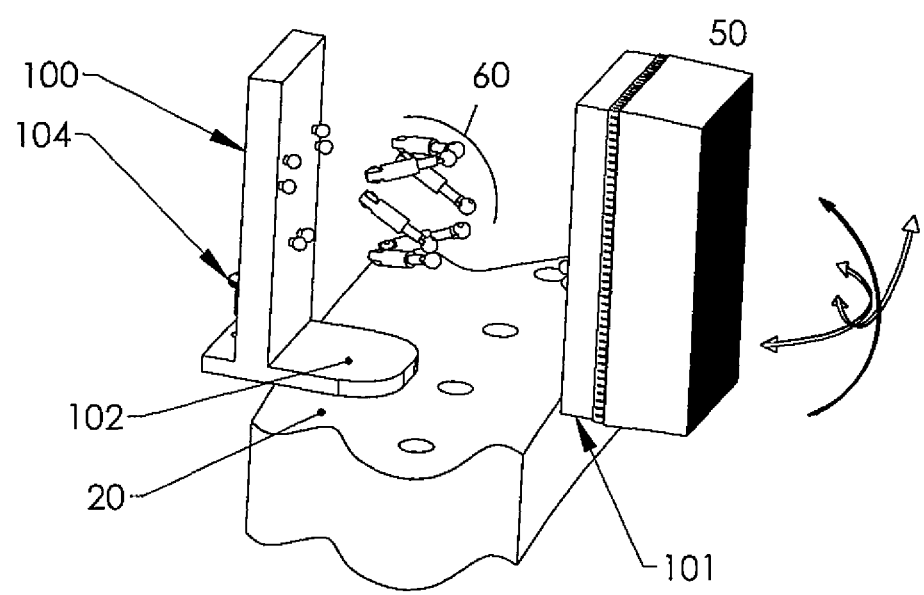
FIG. 16 is an exploded view of the X-ray detector module steering assembly of FIG. 15.

Other arrangements for the actuators may be used. For example, a Stewart platform arrangement may be used to adjust the position of an X-ray detector module. FIGS. 15-16 show module 50 and a mounting arrangement where plate 101 is coupled to the rear of module 50 and frame 100 with optical seat 102 is secured to backbone 20 with fastener 104. Liner actuators 60 are in a Stewart platform configuration and are pivotably connected on one end to frame 100 and pivotably connected on the other end to back plate 101. In this version, all the actuators move the back plate and thus the X-ray detector module relative to frame 100 and backbone 20.

A Stewart platform or hexapod typically includes an array of six linear actuators. The ends of the actuators are free to swivel on their respective mounts at each end. The actuator may be driven by electrical, mechanical, hydraulic, piezoelectric, and micromechanical (MEMS) systems. The inherent stiffness of the actuator assembly when fixed is due to the triangulation mounting of the linear actuators.

Computer controlled algorithms may control the actuators motion individually allowing precise positioning in six axis, X, Y, Z, and tip, tilt and yaw.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. An X-ray system comprising:
   a plurality of X-ray detector modules;
   a backbone for positioning said detector modules relative to an X-ray source;
   a mount for each of said detector modules, the mount coupled to the backbone;
   one or more actuators between the mount and the detector module for individually adjusting the detector module relative to the mount for aligning the detector module; and
   a plate with a rocker member attached behind the module, the mount including a frame with cradle surfaces for the rocker member.

2. The system of claim 1 including a Y-motion actuator between the frame and the rocker member.

3. The system of claim 1 including a tip actuator between the plate and the frame for pivoting the rocker member in the cradle surfaces.

4. The system of claim 1 further including one or more actuators between the frame and the backbone for moving the frame and module relative to the backbone.

5. The system of claim 4 including a tilt actuator between the frame and the backbone for adjusting the frame relative to the backbone.

6. The system of claim 4 in which the frame includes a seat with a post and the backbone includes a socket receiving the post therein.

7. The system of claim 6 further including a Z-axis actuator in the socket for adjusting the frame relative to the backbone.

8. The system of claim 1 in which the mount, the module, and the actuators are configured as a Stewart platform.

9. The system of claim 8 further including a plate coupled to the detector module and a frame member coupled to the backbone with the actuators extending between the plate and the frame.

10. The system of claim 1 in which the X-ray detector module includes a 2-D anti-scatter grid, scintillator material, and a photodiode array.

11. An X-ray system detector module steering system comprising:
    a mount for a detector module attachable to a backbone;
    one or more actuators configured to adjust the detector module relative to the mount and/or to adjust the mount relative to the backbone; and
    a plate with a rocker member attached behind the detector module, the mount including a frame with cradle surfaces for the rocker member.

12. The system of claim 11 in which the mount and actuators are configured to adjust the module relative to the mount and to adjust the mount relative to the backbone.

13. The system of claim 11 including a Y-motion actuator between the frame and the rocker member.

14. The system of claim 11 including a tip actuator between the plate and the frame for pivoting the rocker member in the cradle surfaces.

15. The system of claim 11 further including one or more actuators between the frame and the backbone for moving the frame and detector module relative to the backbone.

16. The system of claim 15 including a tilt actuator between the frame and the backbone for adjusting the frame relative to the backbone.

17. The system of claim 15 in which the frame includes a seat with a post and the backbone includes a socket receiving the post therein.

18. The system of claim 17 further including a Z-axis actuator in the socket for adjusting the frame relative to the backbone.

19. The system of claim 11 in which the mount, the module, and the actuators are configured as a Stewart platform.

20. The system of claim 19 further including a plate coupled to the detector module and a frame member coupled to the backbone with the actuators extending between the plate and the frame.

21. The system of claim 11 in which the X-ray detector module includes a 2-D anti-scatter grid, scintillator material, and a photodiode array.

22. An X-ray system comprising:
    a plurality of X-ray detector modules;
    a backbone for positioning said detector modules relative to an X-ray source;
    a mount for each of said detector modules, the mount coupled to the backbone; and
    one or more actuators between the mount and the detector module for individually adjusting the detector module relative to the mount for aligning the detector module, wherein the mount, the module, and the one or more actuators are configured as a Stewart platform.

23. An X-ray system detector module steering system comprising:
    a mount for a detector module attachable to a backbone; and
    one or more actuators configured to adjust the detector module relative to the mount and/or to adjust the mount relative to the backbone, wherein the mount, the module, and the one or more actuators are configured as a Stewart platform.

24. An X-ray system comprising:
    a plurality of X-ray detector modules;
    a backbone for positioning said detector modules relative to an X-ray source;
    a mount for each of said detector modules, the mount coupled to the backbone;
    one or more actuators between each mount and each detector module for individually adjusting each detector module relative to its mount thereby aligning each detector module; and a plate with a rocker member attached behind each module, each mount including a frame with cradle surfaces for the rocker member.

* * * * *